(12) United States Patent
Clawson

(10) Patent No.: US 6,863,898 B2
(45) Date of Patent: Mar. 8, 2005

(54) METHOD AND COMPOSITION FOR TREATING HAIRY HOOF WARTS

(76) Inventor: Michael D. Clawson, 19645 E. Elliot Rd., Mesa, AZ (US) 85212

( * ) Notice: Subject to any disclaimer, the term of this patent is extended or adjusted under 35 U.S.C. 154(b) by 144 days.

(21) Appl. No.: 10/294,961

(22) Filed: Nov. 14, 2002

(65) Prior Publication Data

US 2004/0096521 A1 May 20, 2004

(51) Int. Cl.⁷ ............................................. A01N 25/12
(52) U.S. Cl. ..................... 424/405; 424/404; 424/411; 424/421; 424/443; 424/445; 424/694; 424/695; 424/696; 424/682; 424/684; 424/724; 514/165
(58) Field of Search ................................ 424/438, 404, 424/407, 411, 421, 443, 445–449, 694, 695, 696, 682–684, 724; 514/159, 160, 165

(56) References Cited

U.S. PATENT DOCUMENTS 4,199,576 A * 4/1980 Reller et al. ................. 424/230
5,780,064 A 7/1998 Meisters et al.

OTHER PUBLICATIONS

Martindale p. 256–260, 1972.*

Milk's p. 363–369, 452, 556, 1949.*

NAHMS Dairy '96, "Digital Dermatitis on U.S. Dairy Operations", May 1997, 1–28 Booklet.

* cited by examiner

Primary Examiner—Neil S. Levy
(74) Attorney, Agent, or Firm—John D. Lister

(57) ABSTRACT

Hairy hoof warts in animals are treated by topically administering an effective amount of a composition of aspirin or other compound or derivative of salicylic acid that preferably contains at least 50% by weight and more preferably between about 75% and 100% by weight aspirin or other compound or derivative of salicylic acid. A preferred composition includes aspirin, hydrated lime, sodium bentonite, and chalk or iron oxide.

6 Claims, No Drawings

METHOD AND COMPOSITION FOR TREATING HAIRY HOOF WARTS

BACKGROUND OF THE INVENTION

The subject invention relates to a method of and compound for treating and/or preventing hairy hoof warts on animals through the topical application of aspirin or another compound or derivative of salicylic acid to an infected area of an animal's hoof or, as a preventive measure, to an area of an animal's hoof that could be infected.

Hairy hoof warts (papillomatous digital dermatitis), also referred to as digital dermatitis, hairy footwarts, strawberry or raspberry heelwarts or hairy heel warts, is a common disease condition in dairy cows. As set forth in the NAHMS Dairy Study, May 1997, entitled "Papillomatous Digital Dermatitis on U.S. Dairy Operations, 47 percent of dairy herds across the United States reported the occurrence of papillomatous digital dermatitis. The study further states that: Papillomatous digital dermatitis (digital dermatitis or footwarts) has been recognized as an emerging disease condition in dairy cows. It was first reported in Italy in 1974 (Cheli and Mortellaro, 1974), and since that time has been reported from countries around the world (Blowey, 1988). In the U.S., it was first reported as lameness outbreaks in New York dairy herds (Rebhun and others, 1980) and, since the late 1980's, as an important cause of bovine lameness (Read and other, 1992).

Clinically, digital dermatitis typically appears as a lameness outbreak of variable severity within dairy herds. It is a superficial skin disease of the bovine digit with variable presentation, depending on the stage of the lesion, from painful, moist, strawberry-like lesions to raised, hairy, wart-like lesions (Read and others, in press). These lesions, usually located on the rear of the foot between the bulbs of the heel, have been referred to by several names, including hairy footwarts, strawberry (or raspberry) heelwarts, and digital dermatitis. Early lesions usually respond to topical antibiotic treatment, although they may recur later."

The study goes on to indicate that a high morbidity rate is seen in some herds with a resulting severe lameness in affected cows and associated losses in milk production, reproductive efficiency, and body weight The resulting severe lameness in affected cows and the associated losses in milk production, reproductive efficiency, and body weight together with the treatments costs have created significant economic losses for affected dairy producers. While the study indicates that the cause of digital dermatitis is not fully understood, the study goes on to indicate that digital dermatitis is a contagious disease, based on the spread of disease regionally, high levels of disease within affected herds, within-herd spread after introduction of affected cattle, and higher prevalence in younger cows and that large herd size, the amount of moisture in corrals where cows walk, and the introduction of dairy replacement heifers are contributing factors to disease occurrence.

As set forth in U.S. Pat. No. 5,780,064, antibiotics have been tried in the treatment or prevention of hairy hoof warts. However, while the use of antibiotics can be effective, the use of antibiotics has several drawbacks. Antibiotics are expensive and there is concern that the use of antibiotics to treat dairy cows may result in the presence of antibiotic residues in the animal or its milk. In addition, the development of antibiotic resistant bacteria strains may make such treatments less effective. Chemical based germicides have also been used, but according to U.S. Pat. No. 5,780,064, many of these chemical based germicides are expensive and had not been proven to be effective against papillomatous digital dermatitis. U.S. Pat. No. 5,780,064, discloses an aqueous germicidal composition for the treatment or prevention of infectious diseases of the hoof in animals, comprising a copper salt, a quaternary ammonium compound, and a peroxide and the topical administration of such compositions to affected disease areas.

The subject invention provides an inexpensive, easy to use, highly effective, method of and composition for treating and/or preventing hairy hoof warts on animals through the topical application of a composition that is a compound or derivative of salicylic acid, preferably aspirin, or a composition containing aspirin or another compound or derivative of salicylic acid.

SUMMARY OF THE INVENTION

In the method of the subject invention for treating and/or preventing hairy hoof warts, a composition that is aspirin or another compound or derivative of salicylic acid or a composition containing aspirin or another compound or derivative of salicylic acid is topically administered to the hoof of the animal. Preferably, the composition topically administered to the hoof contains at least 75% by weight aspirin or other compound or derivative of salicylic acid. Aspirin is a well-known white crystalline compound or derivative [$C_9H_8O_4$ or $CH_3COOC_6H_4COOH$] of salicylic acid that is normally used as an antipyretic and analgesic and called also acetylsalicylic acid. Aspirin is a member of a group of drugs called salicylates. Other salicylates include sodium salicylate, sodium thiosalicylate, choline salicylate, and magnesium salicylate. While compounds or derivatives of these other salicylates have not been tested (only aspirin has been tested), it is believed that compounds or derivatives of these other salicylates may also function as or similar to aspirin as a treatment arid/or preventive measure for hairy hoof warts.

A composition of the subject invention for treating and/or preventing hairy hoof warts contains aspirin and hydrated lime and may also contain sodium bentonite and/or chalk or iron oxide. The hydrated lime functions as a germicide and disinfectant. When used in the composition, the sodium bentonite functions as a filler that absorbs moisture. When used in the composition, the chalk or iron oxide functions as a filler that may be used to achieve a desired coloration for the aspirin composition. The aspirin composition of the subject invention does not bum or irritate the treated area and, preferably, the aspirin composition of the subject invention is totally antibiotic free.

In testing the method of the subject invention on cows with hairy hoof warts, an aspirin composition (100% aspirin powder) was administered to the infected hoof by incorporating the aspirin into a conventional footwrap and wrapping the footwrap about an animal's hoof so that the aspirin was applied to an infected area of an animal's hoof. The aspirin composition of the subject invention that includes about 75% by weight aspirin powder, about 5% by weight hydrated lime, about 15% by weight sodium bentonite, and about 5% by weight chalk was also tested in the same manner. With the application of the aspirin compositions to the infected hoof areas by this method, the infection progressively diminished and the hairy hoof warts were typically healed within about fourteen days.

Aspirin has also been administered to infected areas of an animal's hoofs by applying a liquid composition of aspirin, sodium bentonite and water to the infected areas of the animal's hoofs through the use of footbaths. The liquid composition was made by adding five pounds of a composition containing 20% by weight aspirin and 80% by weight sodium bentonite to twenty-five gallons of water. While the concentration of aspirin administered to the infected areas of the hoofs was considerably less than the 100% and the 75% by weight concentrations applied through the use of footwraps, the application of the aspirin to the infected hoofs through the use of a liquid incorporating aspirin in a footbath promoted the healing of the hairy hoof warts, but over a longer period of time. A liquid composition of only aspirin and water has also been used in a footbath to treat and/or prevent hairy hoof warts. It is contemplated that compounds or derivatives of salicylic acid other than aspirin can be used in these liquid compositions and that liquid compositions incorporating aspirin or other compounds or derivatives of salicylic acid can also be administered to the hoofs as a spray.

DESCRIPTION OF THE PREFERRED EMBODIMENTS

In the method of the subject invention for treating anchor preventing hairy hoof warts, an aspirin composition of 100% aspirin, a composition of another compound or derivative of salicylic acid of 100% of the other compound or derivative, an aspirin containing composition, or a composition containing another compound or derivative of salicylic acid is administered in an effective amount to an infected area of an animal's hoof or, as a preventive measure, to an area of an animal's hoof that could be infected. In a preferred embodiment of the method of the subject invention, the composition of or containing aspirin or another compound or derivative of salicylic acid is incorporated into a conventional footwrap, such as but not limited to a footwrap sold by Minnesota Mining and Manufacturing under the trade designation "VetWrap". The footwrap is then applied to an animal's hoof with the composition being applied to the infected area of the hoof or, as a preventive measure, to an area of potential hoof infection. In tests, 23 cubic centimeters of a 100% powdered aspirin composition or a preferred aspirin composition of the subject invention which consisted of about 75% by weight powdered aspirin, about 5% by weight hydrated lime, about 15% by weight sodium bentonite, and about 5% by weight chalk, was incorporated into a conventional footwrap. The footwrap was then wrapped about the animal's hoof with the aspirin composition being applied to the infected area of the hoof. The footwrap was left on the hoof for a period of about fourteen days. While this treatment procedure proved successful in healing even severe hairy hoof wart infections, if necessary, the procedure can be repeated until an infection is fully healed.

While the concentration of aspirin or other compound or derivative of salicylic acid administered to infected areas or potential areas of infection of an animal's hoofs will typically be considerably less than the 50% to 100% by weight concentrations typically applied through the use of footwraps, the aspirin or other compound or derivative of salicylic acid can be administered via a footbath or spray to the infected areas of an animal's hoofs or areas of an animal's hoofs susceptible to infection through the use of a liquid e.g. an aqueous composition, incorporating aspirin or other compound or derivative of salicylic acid. An example of a composition that may be used to make an aqueous composition for footbaths to treat and/or prevent hairy hoof warts contains 20% by weight aspirin and 80% by weight sodium bentonite. The liquid composition for the footbath may be made by adding five pounds of the 20% by weight aspirin and 80% by weight sodium bentonite composition to twenty-five gallons of water. While only aspirin has been used, it is contemplated that another compound or derivative of salicylic acid may be substituted for the aspirin in this composition and that the percentages by weight of aspirin or other compound or derivative of salicylic acid and sodium bentonite can be varied, e.g. about 20% to about 40% by weight aspirin or other compound or derivative of salicylic acid and about 60% to about 80% by weight sodium bentonite. It is also contemplated that the relative amount of water or other liquid mixed with the aspirin or other compound or derivative of salicylic acid and bentonite composition can be more or less than that specified above to adjust the viscosity of the liquid composition for the footbath, e.g. to form a thicker or thinner slurry. The sodium bentonite may facilitate the application of the composition to the hoof of an animal by helping to adhere the composition to the hoof of the animal, e.g. as a thin film, after the animal passes through the footbath. While not preferred, a liquid composition of only aspirin or other compound or derivative of salicylic acid and water may be used in a footbath or spray to treat and/or prevent hairy hoof warts.

Preferred aspirin compositions of the subject invention include about 75% or more aspirin by weight plus other ingredients such as but not limited to hydrated lime, sodium bentonite and chalk or iron oxide. A preferred aspirin composition of the subject invention includes:

| Ingredient | Percent by Weight |
| --- | --- |
| Powdered Aspirin | about 75% to about 80% |
| Hydrated Lime | about 5% to about 10% |
| Sodium Bentonite | about 5% to about 20% |
| Chalk or Iron Oxide | 0% to about 5% |

It is contemplated that another compound or derivative of salicylic acid may be substituted for the aspirin in this composition.

While an aspirin composition of 100% aspirin used in the method of the subject invention appeared to achieve the best results, an aspirin composition such as the composition set forth immediately above will also heal hairy hoof wart infections with substantially the same effectiveness as the 100% aspirin composition. Since hydrated lime, sodium bentonite, and chalk or iron oxide are less expensive than powdered aspirin, a composition such as that set forth immediately above with from about 75% to about 80% by weight powdered aspirin or other compound or derivative of salicylic acid provides a cost savings without appreciably affecting the effectiveness of the treatment. In addition, hydrated lime is a mild germicide and disinfectant and may be beneficial to the healing process in this regard. Sodium bentonite is a commonly used filler or carrier for drugs that absorbs moisture and the ability of the sodium bentonite to absorb moisture from an infected area of a hoof may also be beneficial to the healing process. When used, the chalk or iron oxide is used as a filler and to achieve a desired coloration of the composition.

The use of an aspirin composition of the subject invention, which included about 60% by weight powdered aspirin, in the method of the subject invention was less effective than the aspirin composition of the subject invention containing from about 75% to about 80% powdered aspirin and the healing process was prolonged. The use of an aspirin composition of the subject invention, which included about 50% by weight powdered aspirin, in the method of the subject invention even further prolonged the healing process. Other compositions of the subject invention include:

| Ingredients | Percent by Weight |
|---|---|
| Powdered Aspirin | about 60% to about 75% |
| Hydrated Lime | about 5% to about 10% |
| Sodium Bentonite | about 10% to about 35% |
| Chalk | 0% to about 5% |
| Powdered Aspirin | about 50% to about 60% |
| Hydrated Lime | about 5% to about 10% |
| Sodium Bentonite | about 25% to about 45% |
| Chalk | 0% to about 5% |

It is contemplated that another compound or derivative of salicylic acid may be substituted for the aspirin in this composition.

The following are examples of powdered aspirin, hydrated lime, sodium bentonite, chalk, and iron oxide that may be used in the compositions of the subject invention. A powdered aspirin sold by Bimeda Incorporated of Le Sueur, Minn., under the trade name "aspirin powder". A hydrated lime sold by Standard Lime Products Company of Riverside, Calif., under the trade designation "high calcium hydrated lime type N". A sodium bentonite sold by Western Clay Company of Aurora, Utah, under the trade designation "sodium bentonite". A chalk sold by American Tool Company of Wilington, Ohio, under the trade designation "chalk". An iron oxide sold by Arizona Oxides of El Mirage, Ariz. under the trade designation "CAS #1309-37-1 crystalline silica.

In describing the invention, certain embodiments have been used to illustrate the invention and the practices thereof. However, the invention is not limited to these specific embodiments as other embodiments and modifications within the spirit of the invention will readily occur to those skilled in the art on reading this specification. Thus, the invention is not intended to be limited to the specific embodiments disclosed, but is to be limited only by the claims appended hereto.

What is claimed is:

1. A method for treating hairy hoof warts in animals, comprising:

topically administering composition to an infected area of a hoof of animal; the composition comprising between about 50% and about 75% by weight aspirin; between about 5% and about 10% by weight hydrated lime; and between 15% and 45% by weight sodium bentonite as a filler and to absorb moisture from the infected area of hoof.

2. The method of claim 1 for the treating hairy hoof warts in animals, wherein:

the composition is in a dry powder form.

3. The method of claim 1 for the treating hairy hoof warts in animals, wherein:

the composition is in a dry powder form and is applied through the use of a footwrap.

4. A method for treating hairy hoof warts in animals, comprising:

topically administering a composition to an infected area of a hoof of an animal; the composition comprising between about 75% and about 80% by weight aspirin; between about 5% and about 10% by weight hydrated lime; and between 5% and 20% by weight sodium bentonite as a filler and to absorb moisture from the infected area of hoof.

5. The method of claim 4 for the treating hairy hoof warts in animals, wherein:

the composition is in a dry powder form.

6. The method of claim 4 for the treating hairy hoof warts in animals, wherein:

the composition is in a dry powder form and is applied through the use of a footwrap.

\* \* \* \* \*